US009464265B2

United States Patent
Osawa et al.

(10) Patent No.: US 9,464,265 B2
(45) Date of Patent: Oct. 11, 2016

(54) INCUBATOR FOR ISOLATOR

(75) Inventors: Shinji Osawa, Funabashi (JP); Tetsuya Miyoshi, Tatebayashi (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 1070 days.

(21) Appl. No.: 12/281,534

(22) PCT Filed: Mar. 1, 2007

(86) PCT No.: PCT/JP2007/053946
§ 371 (c)(1),
(2), (4) Date: Jan. 14, 2009

(87) PCT Pub. No.: WO2007/102399
PCT Pub. Date: Sep. 13, 2007

(65) Prior Publication Data
US 2009/0221064 A1 Sep. 3, 2009

(30) Foreign Application Priority Data

Mar. 6, 2006 (JP) ................................ 2006-059305

(51) Int. Cl.
| C12M 1/00 | (2006.01) |
| C12M 3/00 | (2006.01) |
| C12M 1/12 | (2006.01) |
| C12M 1/34 | (2006.01) |

(52) U.S. Cl.
CPC ............. *C12M 41/14* (2013.01); *C12M 37/00* (2013.01); *C12M 41/34* (2013.01)

(58) Field of Classification Search
CPC ..... C12M 37/00; C12M 41/14; C12M 41/34
USPC ......... 435/286.1–286.6, 289.1, 303.1, 303.2, 435/287.1, 287.3, 305.1, 285.1
See application file for complete search history.

(56) References Cited

U.S. PATENT DOCUMENTS

| 4,336,329 A | * | 6/1982 | Hesse et al. ....................... 435/3 |
| 4,696,902 A | * | 9/1987 | Bisconte .................... 435/286.2 |
| 5,173,258 A | * | 12/1992 | Childers .......................... 422/27 |

(Continued)

FOREIGN PATENT DOCUMENTS

| EP | 1471138 | 10/2004 |
| JP | 4-45784 | 2/1992 |

(Continued)

OTHER PUBLICATIONS

Takagi, English translation of JP2006-014675, Jan. 2006.*

(Continued)

*Primary Examiner* — Michael Marcheschi
*Assistant Examiner* — Shanta G Doe
(74) *Attorney, Agent, or Firm* — Kratz, Quintos & Hanson, LLP

(57) ABSTRACT

There is provided an incubator for an isolator, which is capable of reliably sterilizing a cultivation room of the incubator, a gas supply pipe and a sampling pipe. An incubator 1 for an isolator 40 includes a gas concentration control pipe 16 provided to communicate to a cultivation room 4 for control of concentration of cultivation gas in the cultivation room 4, a sterile gas circulation pipe 26 for circulating sterile gas from the cultivation room 4 to the gas concentration control pipe 16, and a circulation pump 24 provided in the sterile gas circulation pipe 26.

10 Claims, 10 Drawing Sheets

(56) References Cited

U.S. PATENT DOCUMENTS

| | | | | |
|---|---|---|---|---|
| 6,297,047 | B1* | 10/2001 | Butts | 435/303.1 |
| 7,838,286 | B2* | 11/2010 | Tamaoki et al. | 435/303.1 |
| 2004/0185521 | A1* | 9/2004 | Yoshida | A61L 2/20 435/30 |
| 2005/0084956 | A1* | 4/2005 | Tamaoki et al. | 435/303.1 |
| 2005/0163685 | A1* | 7/2005 | Bissell et al. | 422/292 |
| 2005/0170491 | A1* | 8/2005 | Takagi et al. | 435/287.1 |
| 2005/0186671 | A1* | 8/2005 | Cannon et al. | 435/297.2 |
| 2006/0175245 | A1* | 8/2006 | Gerteis | B04B 3/025 210/372 |

FOREIGN PATENT DOCUMENTS

| | | | |
|---|---|---|---|
| JP | 2004-267064 | * | 9/2004 |
| JP | 2005-237274 | A1 | 9/2005 |
| JP | 2005-278565 | A1 | 10/2005 |
| JP | 2005-278566 | A1 | 10/2005 |
| JP | 2006-014675 | * | 1/2006 |
| WO | 9820106 | | 5/1998 |
| WO | WO2004011593 | * | 2/2004 |
| WO | 2004/028573 | A1 | 4/2004 |
| WO | 2006016620 | | 2/2006 |

OTHER PUBLICATIONS

Kawa, English abs of jp2004-267064, Sep. 2004.*
International Search Report for International Application No. PCT/JP2007/053946 dated Mar. 27, 2007.
European Search Report issued Mar. 13, 2013 in counterpart application No. 07737626.7 (3 pages).
European Office Action, for the Corresponding EP Application No. 07 737 626.7-1501, mailed on May 15, 2015.

* cited by examiner

FIG. 5

| | MANUAL COCK A | ELECTRONIC VALVE B | ELECTRONIC VALVE C | ELECTRONIC VALVE D | ELECTRONIC VALVE E | PUMP |
|---|---|---|---|---|---|---|
| NORMAL MODE | CLOSED | CLOSED | CLOSED | OPENED/CLOSED | OPENED/CLOSED | OFF |
| SAMPLING MODE | OPENED | CLOSED | CLOSED | OPENED/CLOSED | OPENED/CLOSED | OFF |
| STERILIZING MODE | CLOSED | OPENED/CLOSED ※ | CLOSED/OPENED ※ | CLOSED | CLOSED | ON |

※ ELECTRONIC VALVES B AND C ARE ALTERNATELY OPENED.

FIG. 9

|  | MANUAL COCK A | ELECTRONIC VALVE C | ELECTRONIC VALVE D | PUMP |
|---|---|---|---|---|
| NORMAL MODE | CLOSED | CLOSED | OPENED/ CLOSED | OFF |
| SAMPLING MODE | OPENED | CLOSED | OPENED/ CLOSED | OFF |
| STERILIZING MODE | CLOSED | OPENED | CLOSED | ON |

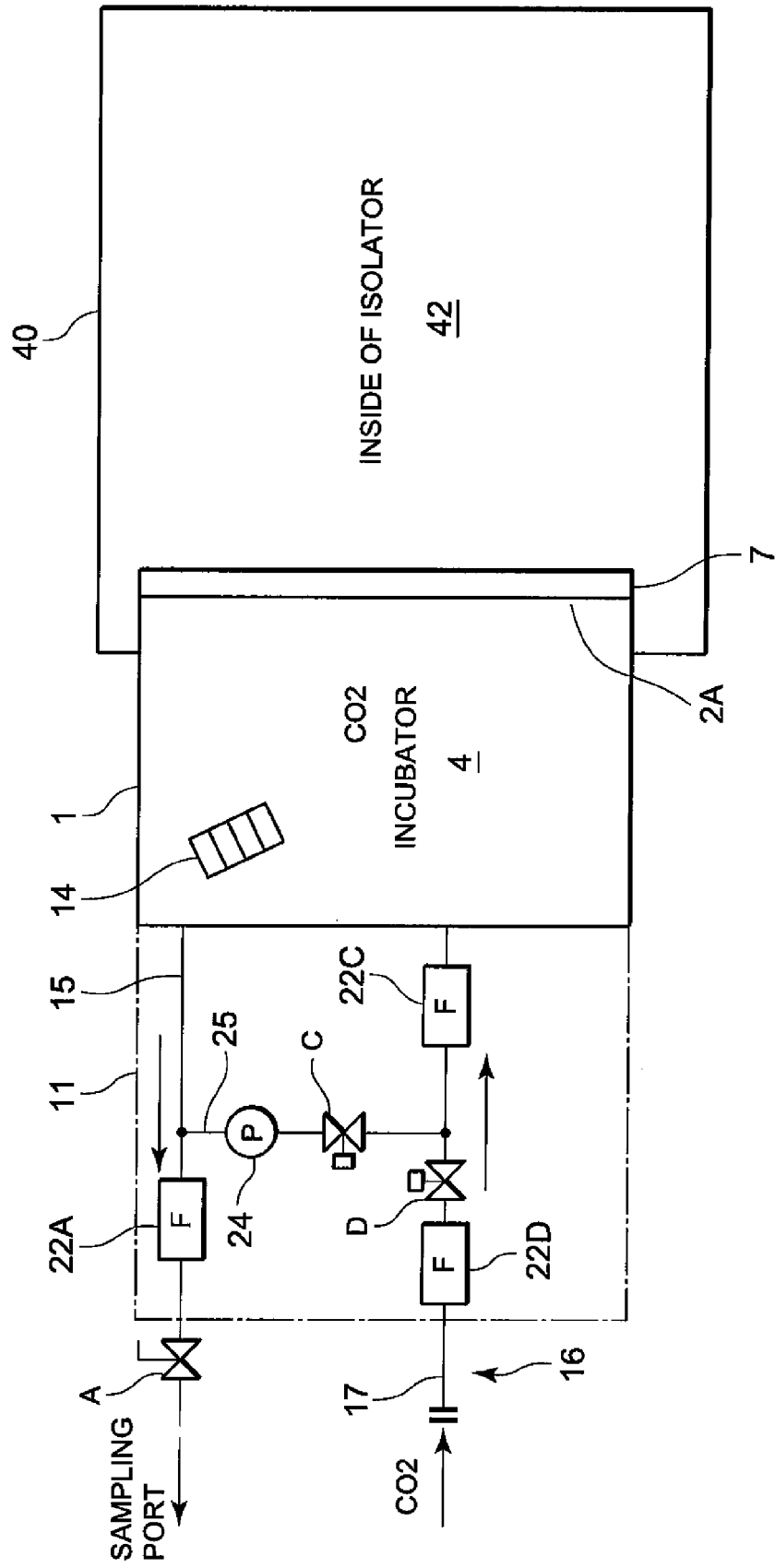

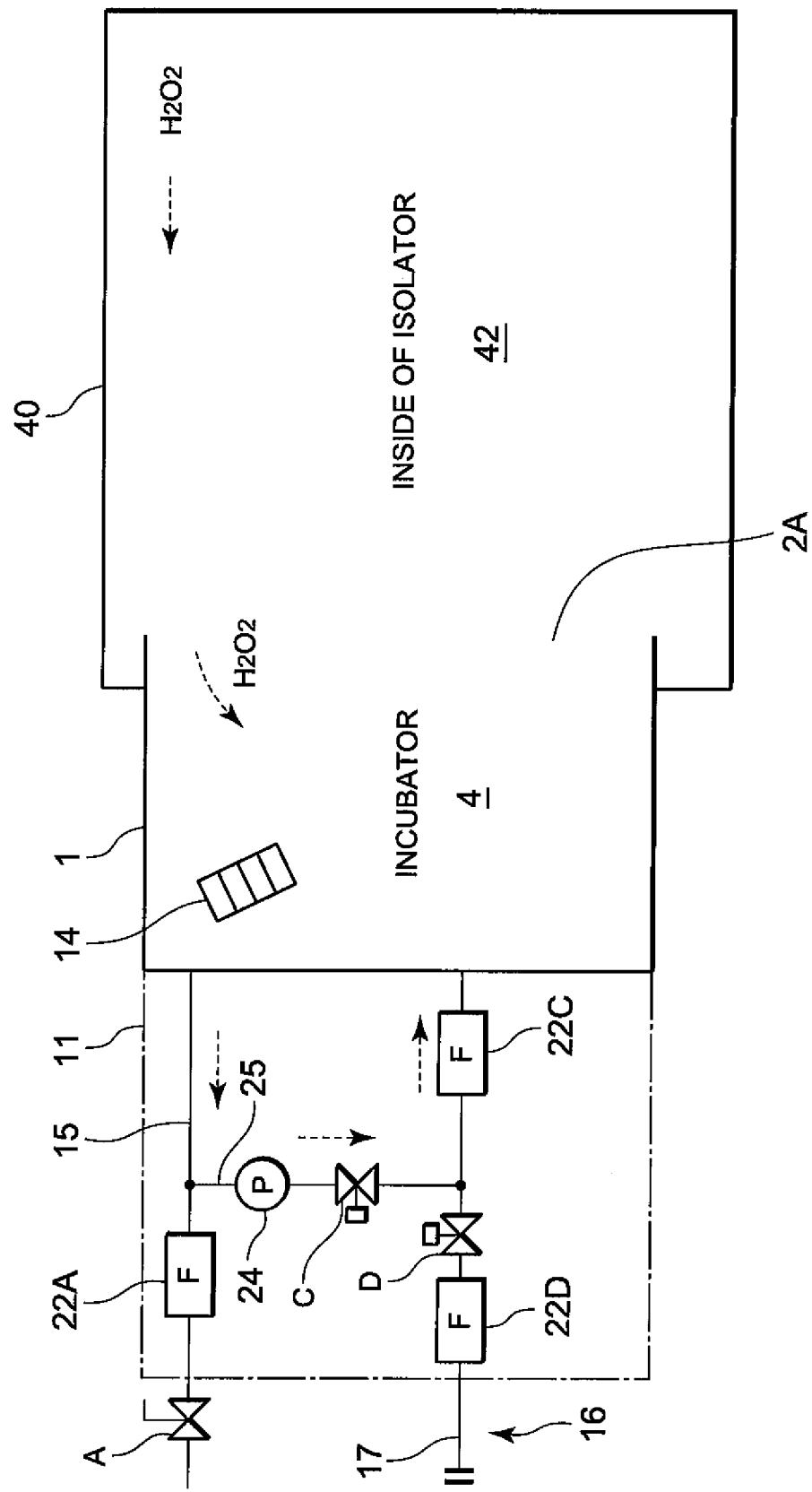

INCUBATOR FOR ISOLATOR

BACKGROUND OF THE INVENTION

1. Field of the Invention

This invention relates to an incubator connected to a chamber of an isolator.

2. Description of the Related Art

In recent years, there have been used isolators of so-called microbiologically controlled environments in which cells (including bacteria and the like) taken from organisms including the human body, animals and so on, or microbes are cultivated in aseptic conditions. The isolators use a plurality of aseptic boxes or aseptic operating boxes (glove boxes) connected in series so that cells or microbes can be cultivated in aseptic conditions. Operations such as cultivation experiments on cells or microbes have been performed by an operator through a glove or similar sterile access device in a chamber of an isolator (see Patent Document 1).

In addition, after an operation such as application of a culture solution to the cells or the microbes cultivated in the chamber of the isolator is performed, the cells or the microbes are cultivated in a cultivation room of an incubator in an aseptic box (see Patent Document 2). In such a cultivation room of the incubator, typically, carbon dioxide gas ($CO_2$) for pH adjustment of culture solution, or nitrogen gas/oxygen gas ($N_2/O_2$) in case of high-oxygen cultivation from low-oxygen cultivation is supplied from a gas supply pipe communicating to the cultivation room of the incubator, so that the cells or the microbes can be cultivated in aseptic conditions.

There is a need to eradicate sundry germs when cell manipulation is not performed in the chamber of the isolator. In other words, when exchanging the cells or the microbes under cultivation experiment in the isolator, if sundry germs are introduced into the chamber or portions of the cells or microbes used in the previous cultivation experiment remains in the chamber, they may have an adverse effect on cells or microbes under next cultivation experiment, which may result in incorrect experimental results. For the purpose of overcome this problem, the chamber is sterilized by supplying and filling the chamber with sterile gas from a sterile gas generating device, which is filled with hydrogen peroxide gas ($H_2O_2$) and equipped within the isolator. Furthermore, the cultivation room of the incubator is sterilized by wiping off it with sterile fluid.

In the meantime, there have been used a cultivating apparatus including isolators, incubators connected to the isolators, and gas supply pipes or sampling pipes. However, if there remain sundry germs intruded into this cultivating apparatus or previously cultivated cells or microbes, they may have an adverse effect on results of next cultivation experiments, which may result in incorrect experimental results. To overcome this problem, this cultivation apparatus sterilizes the remaining sundry gems and so on by naturally circulating sterile gas from chambers of the isolators into cultivation rooms of the incubators.

[Patent Document 1] Japanese Patent Application Publication No. 2001-518816

[Patent Document 2] Japanese Patent Application Publication No. 2005-118021

However, when the sterile gas is naturally circulated from the chambers of the isolators into the cultivation rooms of the incubators, corners in the box-like cultivation boxes have anyway poor gas flow and less circulated sterile gas. This may result in incomplete sterilization of the entire cultivation rooms of the incubators.

In addition, the naturally-circulated sterile gas may not be naturally circulated in the sampling pipes and the gas supply pipes for supplying cultivation gas such as carbon dioxide gas into the cultivation rooms of the incubators. This also may result in inability to sterilize the sampling pipes and the gas supply pipes for supplying cultivation gas such as carbon dioxide gas.

To overcome the above-mentioned problems, it is an object of the invention to provide an incubator for an isolator, which is capable of reliably sterilizing a cultivation room of the incubator, a gas supply pipe and a sampling pipe.

SUMMARY OF THE INVENTION

According to a first aspect of the invention, there is provided an incubator for an isolator connected to a chamber of an isolator, including: a gas concentration control pipe provided to communicate to a cultivation room for control of concentration of cultivation gas in the cultivation room; a sterile gas circulation pipe for circulating sterile gas through the cultivation room to the gas concentration control pipe; and a circulation pump provided in the sterile gas circulation pipe.

According to a second aspect of the invention, the incubator for an isolator further includes a filter provided in the gas concentration control pipe located in the downstream of the sterile gas lower than the circulation pump.

According to a third aspect of the invention, the incubator for an isolator further includes a controller having a sterilizing mode to operate the circulation pump, and a fan for circulating the cultivation gas in the cultivation room, and the controller operates the fan in the sterilizing mode.

According to a fourth aspect of the invention, in the incubator for an isolator, a plurality of gas concentration control pipes for supplying a plurality of kinds of cultivation gas into the cultivation room are located in the downstream of the sterilizing gas lower than the circulation pump, and the controller introduces the sterile gas, which is discharged from the circulation pump, into the gas concentration control pipes alternately.

According to the first aspect of the invention, since the incubator connected to the chamber of the isolator includes the gas concentration control pipe provided to communicate to the cultivation room for control of concentration of cultivation gas in the cultivation room, the sterile gas circulation pipe for circulating sterile gas through the cultivation room to the gas concentration control pipe, and the circulation pump provided in the sterile gas circulation pipe, when the isolator is sterilized by the sterile gas, by operating the circulation pump in the state where the cultivation room of the incubator communicates to the chamber of the isolator, the sterile gas can be circulated from the cultivation room to the gas concentration control pipe. Accordingly, while sterilizing the chamber of the isolator, the gas concentration control pipe in addition to the cultivation room can be also sterilized by the sterile gas.

According to the second aspect of the invention, since the incubator further includes the filter provided in the gas concentration control pipe located in the downstream of the sterile gas lower than the circulation pump, alien substances generated in the circulation pump are absorbed and removed by this filter. This can prevent the alien substances from being introduced into the cultivation room.

According to the third aspect of the invention, since the incubator further includes the controller having the sterilizing mode to operate the circulation pump, by putting the incubator in the sterilizing mode while sterilizing the isolator, the cultivation room and the gas concentration control pipe can be easily sterilized. In particular, since the fan for circulating the cultivation gas in the cultivation room is operated in the sterilizing mode, the sterile gas filling the chamber of the isolator can spread into the cultivation room throughout.

According to the fourth aspect of the invention, when the incubator includes the plurality of gas concentration control pipes for supplying a plurality of kinds of cultivation gas, which are located in the downstream of the sterilizing gas lower than the circulation pump, since the sterile gas, which is discharged from the circulation pump, is alternately introduced into the gas concentration control pipes, it is possible to prevent sterile gas circulation from being biased to any pipe, like simultaneous introduction of the sterile gas into the gas concentration control pipes.

BRIEF DESCRIPTION OF THE DRAWINGS

FIG. 5 is a table showing operation specification of the incubator for the isolator.

FIG. 9 is a table showing operation specification of the incubator for the isolator.

FIG. 10 is a piping diagram (in sampling mode) of the incubator for the isolator of the invention.

FIG. 11 is a piping diagram (in sterilizing mode) of the incubator for the isolator of the invention.

DESCRIPTION OF THE PREFERRED EMBODIMENTS

The most important feature of the present invention is to include a sterile gas circulating pump and a fan for circulating cultivation gas in a sterilizing mode in a cultivation room of an incubator in order to reliably sterilize the cultivation room of the incubator and a gas concentration control pipe. The purpose of reliably sterilizing the cultivation room of the incubator and the gas concentration control pipe can be accomplished by a simple configuration that the sterile gas circulating pump is provided and the fan is operated in the sterilizing mode.

Embodiment 1

Figure 1:
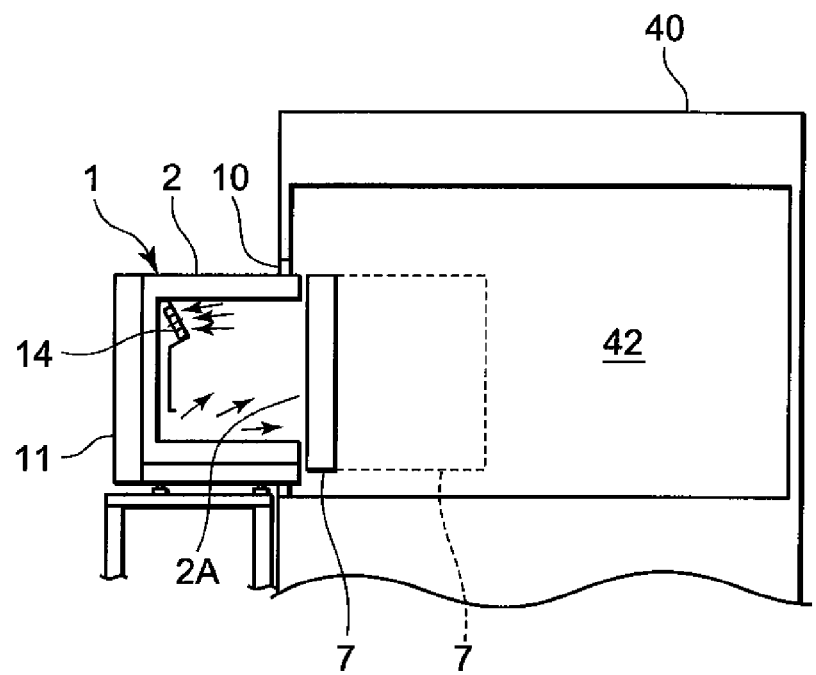
FIG. 1 is a schematic sectional view of an incubator for an isolator according to one embodiment (Embodiment 1) of the present invention.
Figure 2:
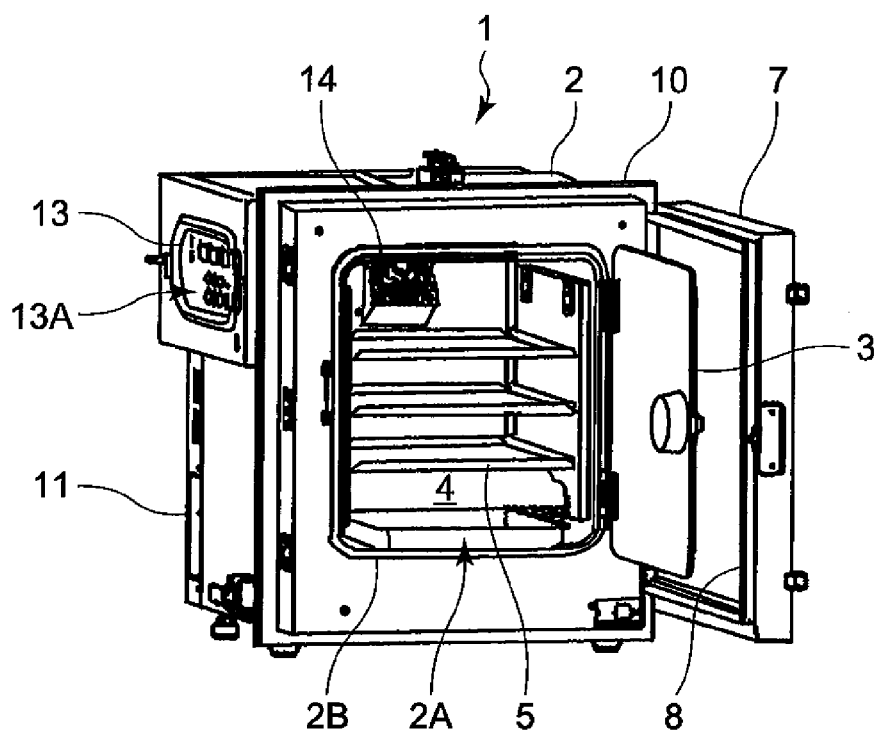
FIG. 2 is a perspective view of the incubator (with an insulating door opened) for the isolator of the invention.
Figure 3:
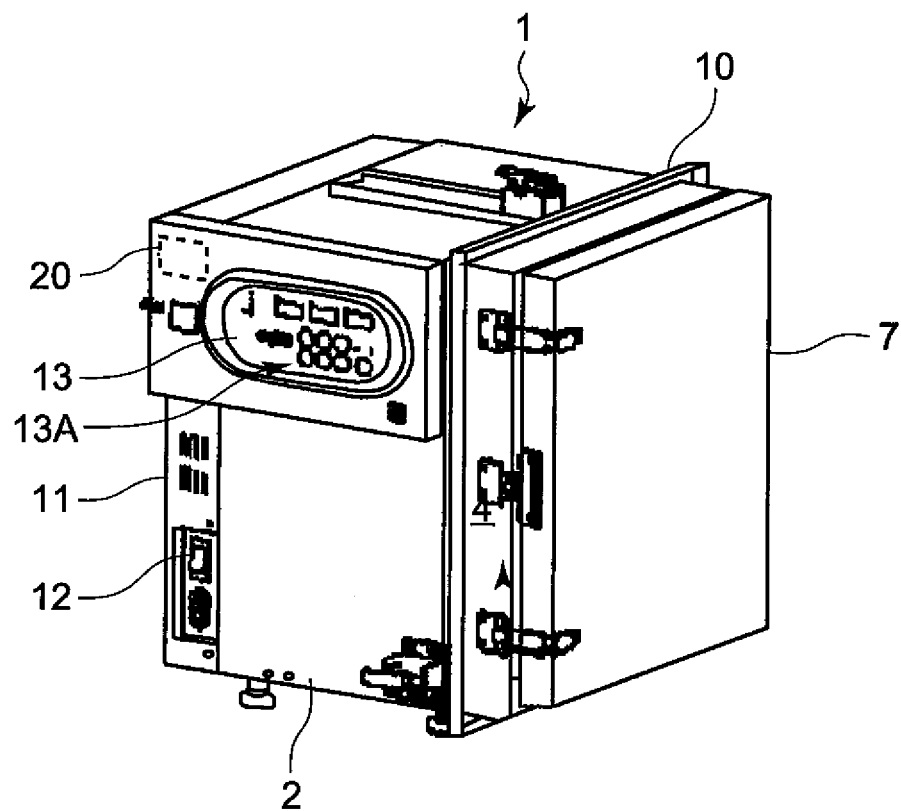
FIG. 3 is a perspective view of the incubator (with an insulating door closed) for the isolator of the invention.

Hereinafter, embodiments of the present invention will be described with reference to the drawings. FIG. 1 is a schematic sectional view of an incubator 1 (cultivation room 4) for an isolator 40 according to one embodiment of the present invention, FIG. 2 is a perspective view of the incubator 1 (with an insulating door 7 opened) for the isolator 40 of the invention, and FIG. 3 is a perspective view of the incubator 1 (with the insulating door 7 closed) for the isolator 40 of the invention.

The incubator 1 for the isolator 40, which is a so-called multi-gas incubator, is attached to a side of the isolator 40, as shown in FIG. 1. The incubator 1 cultivates cells (including bacteria and the like) taken from organisms including the human body, animals and so on, or microbes in aseptic conditions.

In a chamber 42 of the isolator 40, cultivation experiments and the like on cells or microbes are made by an operator through a glove or similar sterile access device. A sterile gas supply device (not shown) is connected to the chamber 42 of the isolator 40 via pipes, and the chamber 42 of the isolator 40 can be sterilized by supplying hydrogen peroxide gas ($H_2O_2$) as sterile gas from the sterile gas supply device into the chamber 42.

The incubator 1 includes an insulating box (not shown), an insulating box body 2 constituted by an inner metal box provided inside the insulating box, and an insulating door 7 that freely communicates/blocks an opening 2A of a cultivation room 4 in the insulating box body 2 to/from the chamber 42 of the isolator 40. In the insulating box body 2, an attachment frame 10 is arranged near the insulating door 7. The attachment frame 10 is provided to project from the insulating box body 2 by a predetermined dimension on the entire circumference of the insulating box body 2.

The attachment frame 10 is configured to fit in an attachment frame hole (not shown) of the isolator 40 under a condition where the insulating door 7 of the incubator 1 is located within the chamber 42 of the isolator 40. In addition, in a condition where the attachment frame 10 of the incubator 1 fits in the attachment frame hole of the isolator 40, the circumference of the attachment frame 10 and the attachment frame hole are sealed by a seal member (not shown) to enclose the chamber 42 of the isolator 40.

In addition, as shown in FIGS. 2 and 3, the incubator 1 is provided with a transparent door 3 (inner door) freely closed/opened to block/unblock the opening 2A of the insulating box body 2. The insulating door 7 is located at the outside of the transparent door 3. The insulating door 7 is an outer door for preventing heat from entering from the opening 2A of the cultivation room 4. The right side of the insulating door 7 is supported to the insulating box body 2 by a hinge in such a manner that the door can be freely opened/closed with respect to the insulating box body 2. A gasket 8 having a magnet is provided around the inner side of the insulating door 7.

The right side of the transparent door 3 is supported to the insulating box body 2 by a hinge in such a manner that the door 3 can be freely opened/closed with respect to the insulating box body 2. The transparent door 3 air-tightly blocks the opening 2A by a gasket 2B provided in the opening 2A of the cultivation room 4. The cultivation room 4 is formed in a space within the insulating box body 2 with the opening 2A blocked by the insulating door 7. When the insulating door 7 and the transparent door 3 are opened from the chamber 42 of the isolator 40, cultivation materials are deposited/drawn in/out the cultivation room 4.

A fan 14 for forcedly circulating cultivation gas in the cultivation room 4 is formed in an upper portion within the cultivation room 4. Ducts (not shown) are formed in the rear and bottom of the cultivation room 4. While the cultivation gas in the cultivation room 4 is absorbed by the fan 14 from an inlet on the rear upper portion communicating to the ducts, the cultivation gas is jetted into the cultivation room 4 from an outlet formed the bottom front portion and the side portion communicating to the ducts. Accordingly, the cultivation is forcedly circulated (arrow indicated by a solid line in FIG. 1).

A machine room 11 including a power switch 12, a manual cock A, electronic valves B, C, D and E (shown in FIG. 4), etc. is provided in the side of the insulating box body 2 (outer side of the cultivation room 4). Also, the machine room 11 includes a gas concentration control pipe 16, a control board (not shown), a board on which electronic components are disposed (not shown), etc., for driving the fan 14 or supplying supply gas such as nitrogen gas or oxygen gas into the cultivation room 4.

The machine room 11 includes the fan 14, the manual cock A, the electronic valves B, C and D, etc. The fan 14 includes a fan, a motor and a shaft (all not shown). The motor is disposed in the machine room 11 and the shaft is connected to the fan from the motor of the machine room 11 through the side of the insulating box body 2.

An operation panel 13 is provided in an outer surface of the incubator 1 located in the outer side of the chamber 42 of the isolator 40. The operation panel 13 is operable from the outside. The operation panel 13 includes a plurality of operation buttons 13A for operating a normal mode, a sterilizing mode, etc. (all not shown). In an inner side of the operation panel 13 is provided a controller 20 (indicated by a dotted line in FIG. 3) including a general purpose microcomputer and a memory for storing various data.

The controller 20 controls a heater (not shown) provided between the insulating box body 2 and the inner box, or the fan 14 to maintain the cultivation room 4 at a temperature suitable for cultivation. Depending on gas concentration in the cultivation room 4, which is detected by a gas concentration measuring sensor provided in the cultivation room 4, the controller 20 controls opening/closing of the electronic valves B, C, D and E (shown in FIG. 4). The control of opening/closing of the electronic valves B, C, D and E by the controller 20 will be described in detail later.

The opening 2A of the insulating box body 2 is opened toward the isolator 40. By opening the insulating door 7 facing the chamber 42 of the isolator 40 from the inner side of the chamber 42, the cultivation room 4 communicates to the chamber 42. In this state, cells cultivated in the cultivation room 4 are extracted into the chamber 42 and the cells operated in the chamber 42 returns to the cultivation room 4. Of course, these operations are performed through a glove attached to the chamber 42.

Figure 4:
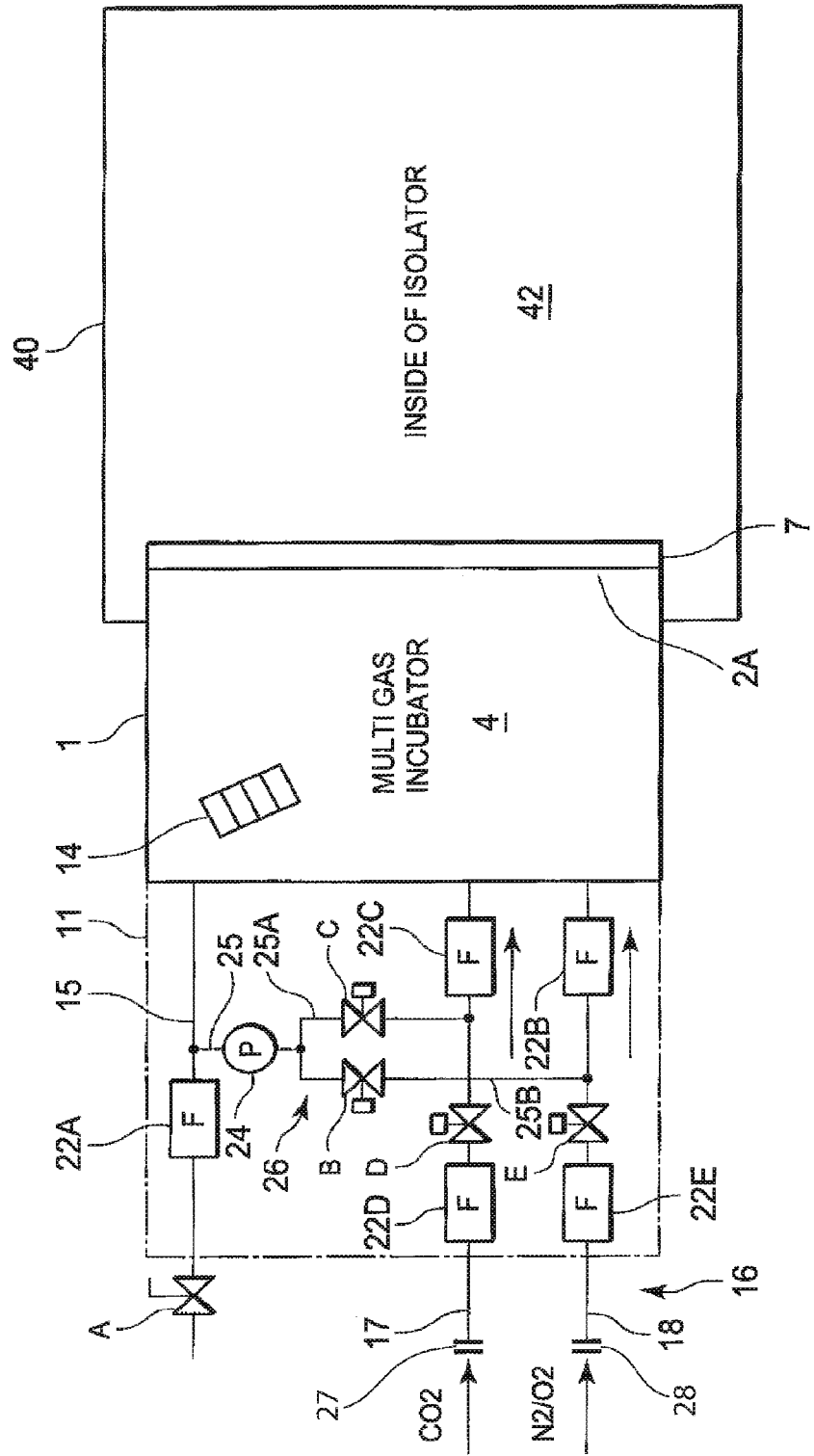
FIG. 4 is a piping diagram (in normal mode) of the incubator for the isolator of the invention.

As shown in FIG. 4, the incubator 1 includes a sampling port (sampling pipe 15) for taking sampling gas. The sampling pipe 15 communicates to the cultivation room 4 of the incubator 1. In addition, a gas concentration control pipe 16 including a first gas supply pipe 17 for supplying carbon dioxide gas ($CO_2$) and a second gas supply pipe 18 for supplying nitrogen gas/oxygen gas communicates to the cultivation room 4 of the incubator 1. In addition, a carbon dioxide supply device (not shown) is connected to an end portion (also referred to as a first connector 27) of the first gas supply pipe 17 and a nitrogen gas/oxygen gas supply device (not shown) is connected to an end portion (also referred to as a second connector 28) of the second gas supply pipe 18.

The sampling pipe 15 is connected with the manual cock A via a filter 22A for obtaining about 100% purity by removing dangerous samples from the cultivation room 4, such as chemicals, microbes or bacteria included in the cultivation gas in the cultivation room 4. When the manual cock A is operated by an operator, gas in the cultivation room 4 may be taken from the sampling pipe 15 to examine its concentration or components.

Like the sampling pipe 15, the first gas supply pipe 17 is connected to the carbon dioxide gas supply device (not shown) via a filter 22C, the electronic valve D and a filter 22D from the cultivation room 4. The controller 20 controls a degree of opening of the electronic valve D to supply a predetermined amount of carbon dioxide gas from the carbon dioxide gas supply device into the cultivation room 4.

Like the sampling pipe 15, the second gas supply pipe 18 is connected to the nitrogen gas/oxygen gas supply device (not shown) via a filter 22B, the electronic valve E and a filter 22E from the cultivation room 4. The controller 20 controls a degree of opening of the electronic valve E to supply a predetermined amount of nitrogen gas/oxygen gas from the nitrogen gas/oxygen gas supply device into the cultivation room 4. The filters 22A, 22D and 22E are constituted by high performance HEPA filers to prevent cells from being leaked out of the cultivation room 4.

That is, the controller 20 controls opening/closing of the electronic valve D to supply the predetermined amount of carbon dioxide gas from the first gas supply pipe 17 into the cultivation room 4. In addition, the controller 20 controls opening/closing of the electronic valve E to supply the predetermined amount of nitrogen gas/oxygen gas from the second gas supply pipe 18 into the cultivation room 4. This creates gas environments (gas concentration) for cell cultivation in the cultivation room 4.

In the meantime, a sterile gas circulation pipe 26 is provided from the sampling pipe 15 to the gas concentration control pipe 16. That is, the sterile gas circulation pipe 26 is provided from the sampling pipe 15 to the first gas supply pipe 17 and the second gas supply pipe 18. In more detail, a circulation pump 24 is provided in the sterile gas circulation pipe 26, a downstream side of the circulation pump 24 is branched to be connected to the first gas supply pipe 17 and the second gas supply pipe 18.

The electronic valve C is provided between the circulation pump 24 and the first gas supply pipe 17, and the electronic valve B is provided between the circulation pump 24 and the second gas supply pipe 18. That is, the sterile gas circulation pipe 26 is provided with a branch pipe 25 (25A and 25B) branched between the incubator 1 and the filter 22A via the circulation pump 24. One branch pipe 25A is connected between the electronic valve D of the first gas supply pipe 17 and the filter 22C via the electronic valve C and the other branch pipe 25B is connected between the electronic valve E of the second gas supply pipe 18 and the filter 22B via the electronic valve B. The sterile gas circulation pipe 26 and the branch pipe 25 are the same pipe.

Alien substances such as dusts generated in the circulation pump 24 are absorbed and removed by these filters 22B and 22C. This can prevent the alien substances from being introduced into the cultivation room 4. The filter 22A may be provided in the upstream upper than a connection portion of the sampling pipe 15 and the sterile gas circulation pipe 26. However, with such arrangement, sterile gas absorbed from the cultivation room 4 may be also adhered, thereby deteriorating a sterilizing effect. Accordingly, the filter 22A is preferably provided in the downstream.

In the meantime, as shown in FIG. 5, the controller 20 has programs of a normal mode, a sampling mode, a sterilizing mode, etc. of the incubator 1, which are stored in a memory of a microcomputer. In the normal mode of the incubator 1, the controller 20 controls the electronic valves B and C to be closed and the electronic valves D and E to opened/closed, and turns OFF (stops) the circulation pump 24.

In the sampling mode, the controller 20 controls the electronic valves B and C to be closed and the electronic valves D and E to opened/closed, and turns OFF the circulation pump 24. In the sterilizing mode, the controller 20 controls the electronic valves B and C to be opened/closed and closed/opened and the electronic valves D and E to closed, and turns ON (operates) the circulation pump 24. In the sterilizing mode, the controller 20 opens/closes the electronic valves B and C alternately.

Next, the normal mode, the sampling mode and the sterilizing mode of the incubator 1 will be described in more detail. It is herein assumed that the insulating door 7 and the manual cock A of the incubator 1 are closed. First, the normal mode of the incubator 1 will be described with reference to FIG. 4. In the normal mode of the incubator 1, when an operation switch 13A (normal mode operation switch) of the operation panel 13 is pushed by an operator, the controller 20 controls the electronic valves B and C to be closed and the electronic valves D and E to opened/closed, turns OFF (stops) the circulation pump 24, and operates the fan 14.

That is, when the controller 20 controls the electronic valves D and E to be opened/closed, the predetermined amount of carbon dioxide gas is supplied from the carbon dioxide gas supply device into the cultivation room 4 of the incubator 1 via the first gas supply pipe 17 and the predetermined amount of nitrogen gas/oxygen gas is supplied from the nitrogen gas/oxygen gas supply device into the cultivation room 4 of the incubator 1 via the second gas supply pipe 18 (arrow-indicated by a solid line in FIG. 4). Accordingly, the predetermined amount of cell cultivation gas is supplied into the cultivation room 4 of the incubator 1.

Based on a detection value of a concentration detecting device, if the concentration of the gas in the cultivation room 4 does not reach a preset concentration, the controller 20 controls opening/closing of the electronic valves D and E provided in the first gas supply pipe 17 and the second gas supply pipe 18 to supply the predetermined amount of carbon dioxide gas and nitrogen gas/oxygen gas into the cultivation room 4 of the incubator 1. In this manner, the controller 20 controls the gas concentration in the cultivation room 4 to create the gas environments (gas concentration) of cell cultivation in the cultivation room 4.

Figure 6:
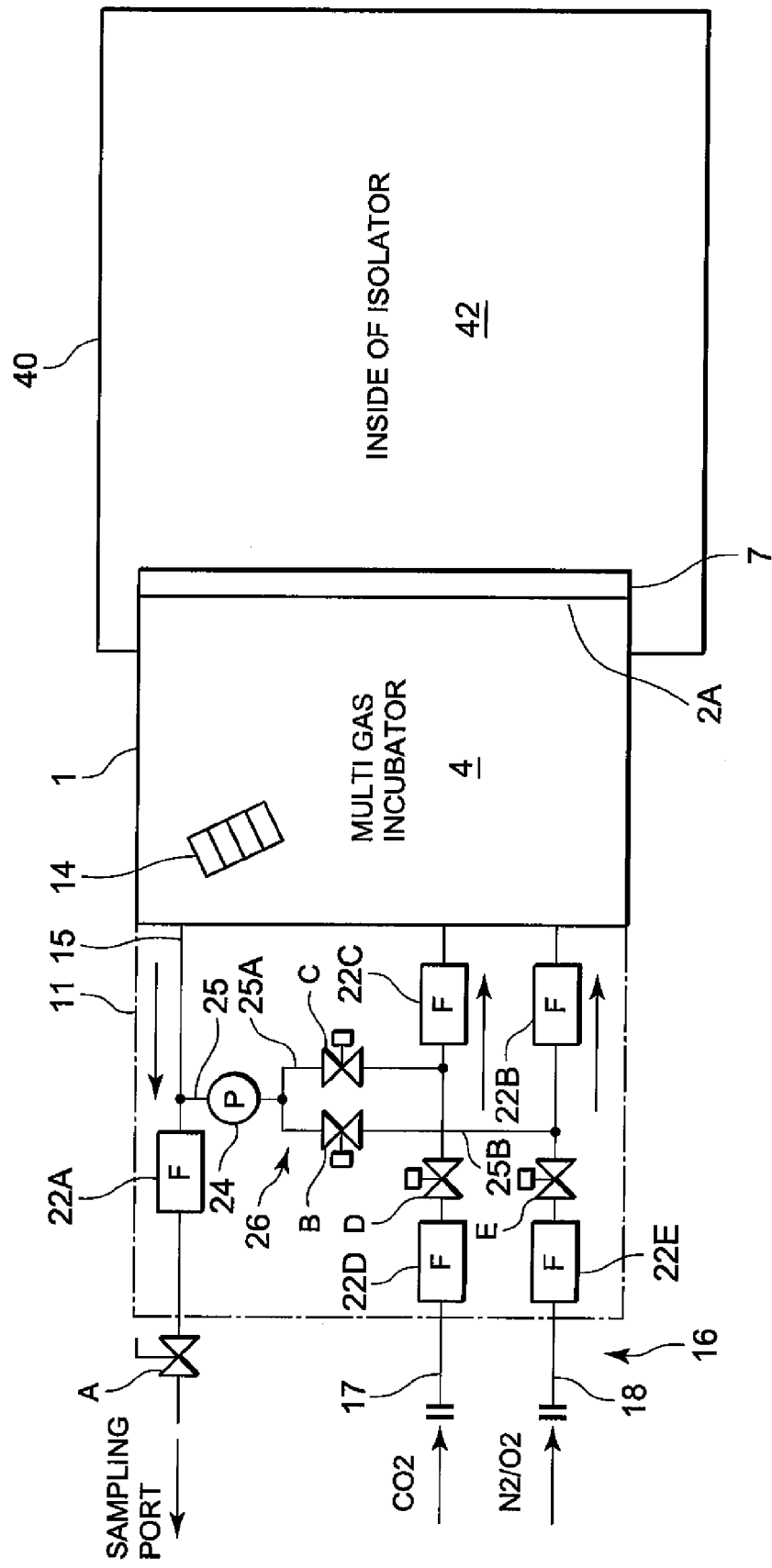
FIG. 6 is a piping diagram (in sampling mode) of the incubator for the isolator of the invention.

Next, the sampling mode of the incubator 1 will be described with reference to FIG. 6. In the sampling mode, the controller 20 operates in the normal mode operation state. That is, when the operation of the incubator 1 is in the normal mode, the manual cock A is opened by the operator. Accordingly, the gas in the cultivation room 4 is taken out of the sampling pipe 15 (arrow indicated by a solid line in FIG. 6), and then the concentration and components of the gas in the cultivation room 4 is analyzed. In this manner, the gas environments in the cultivation room 4 are controlled.

Figure 7:
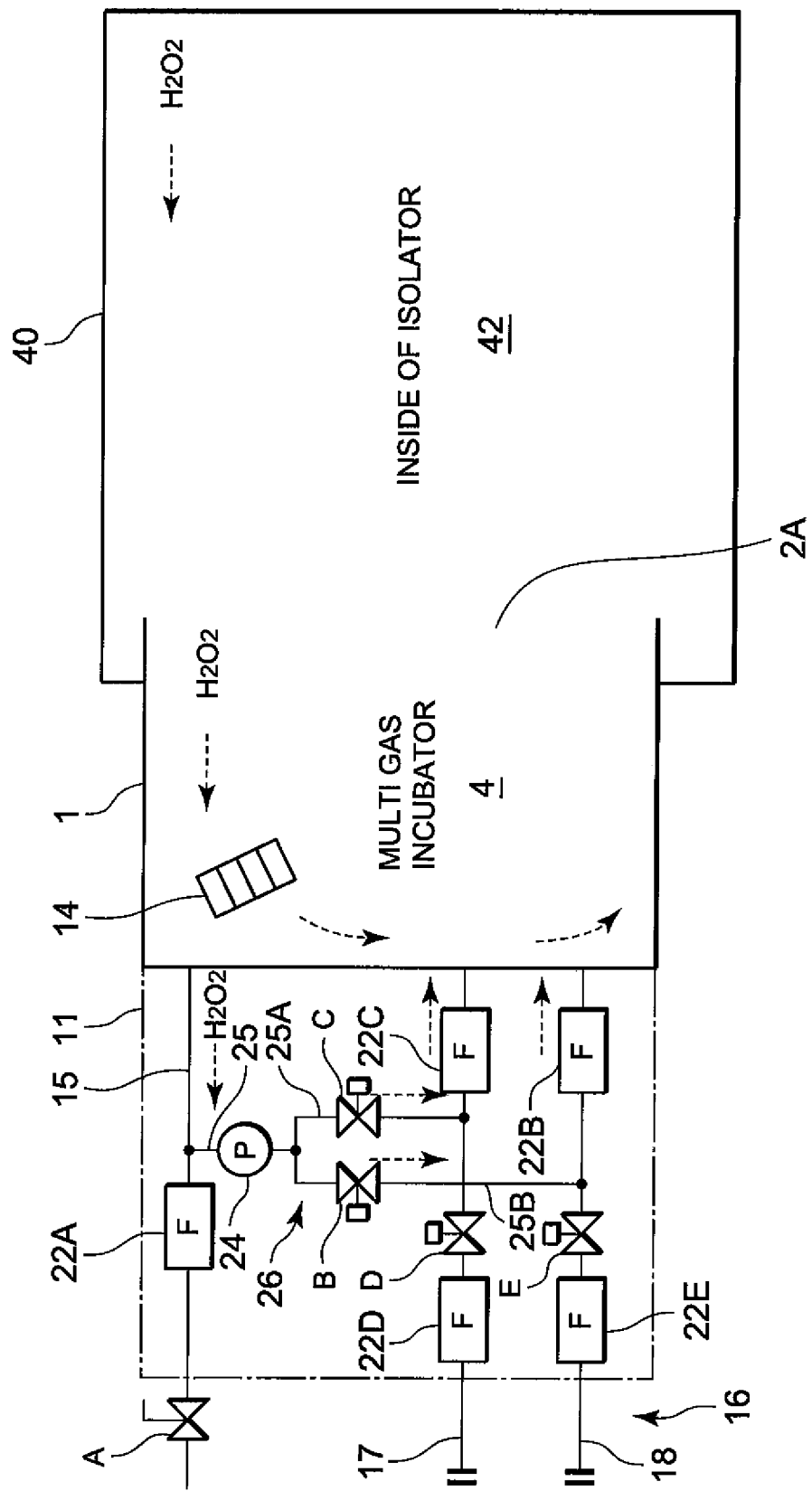
FIG. 7 is a piping diagram (in sterilizing mode) of the incubator for the isolator of the invention.

Next, the sterilizing mode of the incubator 1 will be described with reference to FIG. 7. The cultivation room 4 of the incubator 1 is sterilized at the same time of sterilizing the chamber 42 of the isolator 40. When the cultivation room 4 is sterilized, the operator opens the insulating door 7 and the transparent door 3 of the incubator 1 from the chamber 42 of the isolator 40 and closes the manual cock A in advance. The insulating door 7 and the transparent door 3 of the incubator 1 are not shown in FIG. 7.

In the sterilizing mode operation of the incubator 1, when the sterile gas (hydrogen peroxide gas) is supplied into the chamber 42 of the isolator 40 to sterilize the chamber 42, the operator pushes the operation switch 13A (the sterilizing mode operation switch in this case) of the operation panel 13. When the sterilizing mode operation switch is pushed, the controller 20 controls the electronic valves B and C to be opened/closed and the electronic valves D and E to closed, turns ON the circulation pump 24, and operates the fan 14.

By the operation of the fan 14, the sterile gas in the chamber 42 of the isolator 40 is absorbed in the inlet in the rear upper side from the top of the opening 2A in the cultivation room 4, and the absorbed sterile gas is jetted from the outlet formed in the bottom front portion and the side portion of the cultivation 4. Accordingly, the sterile gas in the chamber 42 of the isolator 40 is forcedly circulated in the cultivation room 4, while spreading up to corners of the cultivation room 4, as indicated by a dotted arrow in FIG. 7, thereby completely sterilizing the cultivation room 4 throughout.

When the controller 20 operates the circulation pump 24, the sterile gas in the cultivation room 4 is absorbed in the sampling pipe 15 and is flown into the branch pipe 25. At this time, the controller 20 controls the electronic valves B and C to be opened/closed alternately at predetermined intervals (in this case, when the electronic valve B is opened, the electronic valve C is closed, and when the electronic valve B is closed, the electronic valve C is opened). That is, the controller 20 alternately opens the electronic valves B and C provided in the branch pipe 25 (in this case, both of the electronic valves B and C are not opened simultaneously, but one of them is opened, and this operation is switched at a predetermined period and is repeated), circulates the sterile gas in the gas concentration control pipe 16 (first and second gas supply pipes 17 and 18) at the downstream alternately. After simultaneously opening both of the electronic valves B and C for a certain time, the electronic valve B or the electronic valve C may be opened and this operation may be switched at a predetermined period and may be repeated. In this case, since both of the electronic valves B and C can not be simultaneously closed, load of the circulation pump 24 is lessened. This is convenient since durability of the circulation pump 24 can be prolonged.

When the sterile gas is simultaneously circulated in the gas concentration control pipe 16 (first and second gas supply pipes 17 and 18), if one of the filter 22B and the filter 22C has larger filter resistance, most of the sterile gas flows into the filter having smaller filter resistance, and thus an sterilizing effect of the pipe having the filter having the larger filter resistance is lowered. Accordingly, the sterile gas is alternately circulated in the first and second gas supply pipes 17 and 18.

The sterile gas introduced from the cultivation room 4 into the branch pipe 25 via the sampling pipe 15 is introduced into one branch pipe 25A and is circulated (arrow indicated by a dotted line in FIG. 7) in the cultivation room 4 via the opened electronic valve C (at this time, the electronic valve B being closed), the first gas supply pipe 17 and the filter 22C. After lapse of predetermined time, the controller 20 closes the electronic valve C and opens the electronic valve B.

The sterile gas introduced from the cultivation room 4 into the branch pipe 25 via the sampling pipe 15 as the electronic valve B is opened by the controller 20 is introduced into the other branch pipe 25B and is circulated (arrow indicated by a dotted line in FIG. 7) in the cultivation room 4 via the opened electronic valve B (at this time, the electronic valve C being closed), the second gas supply pipe 18 and the filter 22B. These operations are alternately performed by a predetermined time interval. Thus, the sterile gas is always circulated in the sampling pipe 15 at the upstream of the circulation pump 24. Accordingly, the sampling pipe 15 at the upstream (at the cultivation room 4 side) upper than a connection point with the sterile gas circulation pipe 26 and the branch pipe 25B and the gas concentration control pipe 16 at the downstream (at the cultivation room 4 side) lower than the connection point are sterilized by the sterile gas.

In this manner, when the isolator 40 is sterilized by the sterile gas, by operating the circulation pump 24 in the state where the insulating door 7 of the incubator 1 is opened to communicate the cultivation room 4 to the chamber 42 of the isolator 40, the sterile gas can be circulated from the cultivation room 4 to the gas concentration control pipe 16 (the first and second gas supply pipes 17 and 18). Accordingly, while sterilizing the chamber 42 of the isolator 40, the gas concentration control pipe 16 in addition to the cultivation room 4 can be also sterilized by the sterile gas.

In addition, since the filters 22C and 22B are respectively in the first and second gas supply pipes 17 and 18 located in the downstream of the sterile gas lower than the circulation pump 24, alien substances generated in the circulation pump 24 (in this case, alien substances generated by abrasion by driving of the circulation pump 24 or alien substances generated during manufacture of the circulation pump 24) can be absorbed and removed by the filters 22C and 22B. This can prevent such alien substances from being introduced into the cultivation room 4. In addition, since the filters 22C and 22B are located in the downstream of the circulation pump 24, the filters 22C and 22B can be prevented from obstructing the circulation of the sterile gas.

In addition, since the controller 20 has the sterilizing mode to operate the circulation pump 24, by putting the incubator 1 in the sterilizing mode while sterilizing the isolator 40, the cultivation room 4 and the gas concentration control pipe 16 can be easily sterilized. In particular, in the sterilizing mode, since the controller 20 operates the fan 14 to circulate the cultivation gas in the cultivation room 4, the sterile gas filling the chamber 42 of the isolator 40 can spread into the cultivation room 4 throughout, thereby reliably sterilizing corners of the cultivation room 4.

In addition, since the sterile gas discharged from the circulation pump 24 is alternately introduced in the gas concentration control pipe 16 (the first and second gas supply pipes 17 and 18) located in the downstream of the sterile gas lower than the circulation pump 24, it is possible to prevent sterile gas circulation from being biased to any pipe, like simultaneous introduction of the sterile gas into the first and second gas supply pipes 17 and 18. Accordingly, it is possible to reliably sterilizing the first and second gas supply pipes 17 and 18.

Embodiment 2

Figure 8:
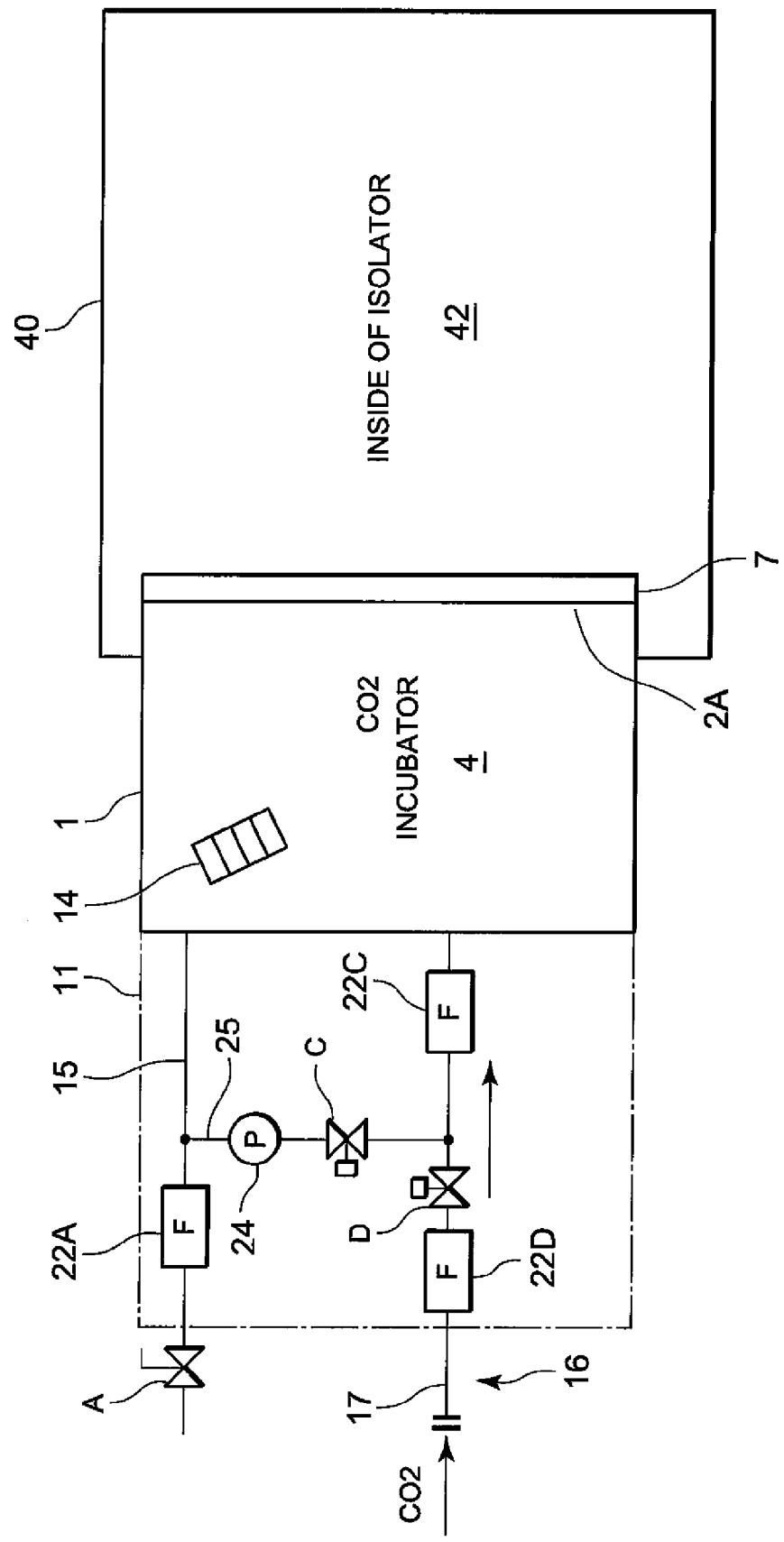
FIG. 8 is a piping diagram (in normal mode) of an incubator for an isolator according to another embodiment (Embodiment 2) of the present invention.

Next, FIG. 8 is a piping diagram of an incubator 1 for an isolator 40 according to another embodiment of the present invention. The incubator 1 for the isolator 40 has substantially the same configuration as the above-described embodiment. Hereinafter, portions different from the above-described embodiment will be described. As shown in FIG. 8, the incubator 1 for the isolator 40 uses only the first gas supply pipe 17 (excluding the second gas supply pipe 18) of the gas concentration control pipe 16 in Embodiment 1. In addition, in Embodiment 2, the electronic valves B and E and the filters 22B and 22E provided incidentally in the second gas supply pipe 18 in Embodiment 1 are excluded.

That is, in the incubator 1 for the isolator 40, the sampling pipe 15 (sampling port) and the gas concentration control pipe 16 (the first gas supply pipe 17) are connected and communicate to the cultivation room 4 of the incubator 1. The branch pipe 25 is connected between the electronic valve D of the first gas supply pipe 17 and the filter 22C via the circulation pump 24 and the electronic valve C from between the incubator 1 and the filter 22A.

As shown in FIG. 9, the Controller 20 has programs of a normal mode, a sampling mode, a sterilizing mode, etc. of the incubator 1, which are stored in a memory of a microcomputer. In the normal mode of the incubator 1, the controller 20 controls the electronic valve C to be closed and the electronic valve D to opened/closed, and turns OFF the circulation pump 24. In the sampling mode, the controller 20 controls the electronic valve C to be closed and the electronic valve D to opened/closed, and turns OFF the circulation pump 24. In the sterilizing mode, the controller 20 controls the electronic valve C to be opened and the electronic valve D to closed, and turns ON the circulation pump 24.

Next, the normal mode, the sampling mode and the sterilizing mode of the incubator 1 will be described in more detail. It is herein assumed that the insulating door 7 and the manual cock A of the incubator 1 are closed. First, the normal mode of the incubator 1 will be described with reference to FIG. 8. In the normal mode of the incubator 1, when an operation switch 13A (normal mode operation switch) of the operation panel 13 is pushed by an operator, the controller 20 controls the electronic valve C to be closed and the electronic valve D to opened/closed, turns OFF the circulation pump 24, and operates the fan 14.

That is, when the controller 20 controls the electronic valve D to be opened/closed, the predetermined amount of carbon dioxide gas is supplied from the carbon dioxide gas supply device into the cultivation room 4 of the incubator 1 via the first gas supply pipe 17 (arrow indicated by a solid line in FIG. 8). Accordingly, the predetermined amount of cell cultivation gas is supplied into the cultivation room 4 of the incubator 1.

Based on a detection value of a concentration detecting device, if the concentration of the gas in the cultivation room 4 does not reach a preset concentration, the controller 20 controls opening/closing of the electronic valve D provided in the first gas supply pipe 17 to supply the predetermined amount of carbon dioxide gas into the cultivation room 4 of the incubator 1. In this manner, the controller 20 controls the gas concentration in the cultivation room 4 to create the gas environments (gas concentration) of cell cultivation in the cultivation room 4.

Next, the sampling mode of the incubator 1 will be described with reference to FIG. 10. In the sampling mode, the controller 20 operates in the normal mode operation state. That is, when the operation of the incubator 1 is in the normal mode, the manual cock A is opened by the operator. Accordingly, the gas in the cultivation room 4 is taken out of the sampling pipe 15 (arrow indicated by a solid line in FIG. 10), and then the concentration and components of the gas in the cultivation room 4 is analyzed. In this manner, the gas environments in the cultivation room 4 are controlled.

Next, the sterilizing mode of the incubator 1 will be described with reference to FIG. 11. The cultivation room 4 of the incubator 1 is sterilized at the same time of sterilizing the chamber 42 of the isolator 40 as described above. When the cultivation room 4 is sterilized, the operator opens the insulating door 7 and the transparent door 3 of the incubator 1 from the chamber 42 of the isolator 40 and closes the manual cock A in advance. The insulating door 7 and the transparent door 3 of the incubator 1 are not shown in FIG. 11.

In the sterilizing mode operation of the incubator 1, when the sterile gas (hydrogen peroxide gas) is supplied into the chamber 42 of the isolator 40 to sterilize the chamber 42, the operator pushes the operation switch 13A (the sterilizing mode operation switch in this case) of the operation panel 13. When the sterilizing mode operation switch is pushed, the controller 20 controls the electronic valve C to be opened and the electronic valve D to closed, turns ON the circulation pump 24, and operates the fan 14. By the operation of the fan 14, the sterile gas in the chamber 42 of the isolator 40 is forcedly circulated in the cultivation room 4, as indicated by a dotted arrow in FIG. 11, thereby completely sterilizing the cultivation room 4 throughout (including its corners).

When the controller 20 operates the circulation pump 24, the sterile gas in the cultivation room 4 is absorbed in the sampling pipe 15 and is flown into the branch pipe 25. The sterile gas flown in the branch pipe 25 is circulated (arrow indicated by a dotted line in FIG. 11) in the cultivation room 4 via the circulation pump 24, the electronic valve C (at this time, the electronic valve D being closed), the first gas supply pipe 17 and the filter 22C.

Thus, the sterile gas is always circulated in the sampling pipe 15 at the upstream of the circulation pump 24. Accordingly, the sampling pipe 15 at the upstream (at the cultivation room 4 side) upper than a connection point with the branch pipe 25 and the branch pipe 25B and the gas concentration control pipe 16 at the downstream (at the cultivation room 4 side) lower than the connection point are sterilized by the sterile gas.

In this manner, when the isolator 40 is sterilized by the sterile gas, by operating the circulation pump 24 in the state where the insulating door 7 and the transparent door 3 of the incubator 1 is opened to communicate the cultivation room 4 to the chamber 42 of the isolator 40, the sterile gas can be circulated from the cultivation room 4 to the gas concentration control pipe 16 (the first gas supply pipe 17). Accordingly, like Embodiment, while sterilizing the chamber 42 of the isolator 40, the gas concentration control pipe 16 in addition to the cultivation room 4 can be also sterilized by the sterile gas.

The present invention is not limited to the above-described embodiments but may be effectively changed and modified in various ways without departing from the spirit and scope of the invention.

What is claimed is:

1. An incubator, to be connected to an isolator and a cultivation gas supply device, the incubator comprising:
a controller;
a cultivation room including a first port, a second port, and a third port, the cultivation room configured to be sterilized by a sterilizing gas supplied from a sterile gas supply device connected to the isolator;
a pipe sterilizing unit wherein the sterilizing gas flows from the second port into a second pipe, through the second pipe to a circulation pump, from the circulation pump into at least one path selected from among path (a) or path (b), wherein path (a) corresponds to a first pipe, through a valve C, to a first filter and then to the first port, wherein path (b) corresponds to a fourth pipe, through a valve B, to a third filter and then to the third port;
a first cultivation gas control unit comprising a first cultivation gas control pipe, the first cultivation gas control pipe including at one end thereof a first connector to connect to a first cultivation gas supply device, and the other end thereof being coupled to the first pipe, wherein the first pipe is between the first filter and the circulation pump, wherein the first cultivation gas control pipe includes a valve D;
a second cultivation gas control unit comprising a second cultivation gas control pipe, the second cultivation gas control pipe including at one end thereof a second connector to connect to a second cultivation gas supply device, and the other end thereof being coupled to the fourth pipe, wherein the fourth pipe is between the third filter and the circulation pump, wherein the second cultivation gas control pipe includes a valve E;
a fan disposed inside the cultivation room; and
a third pipe, having a cock A, connected to the second pipe at a point between the second port and the circulation pump,
wherein the incubator is configured to have:
a first combination of settings corresponding to the cock A being closed, the valve B being closed, the valve C being closed, and the circulation pump being off, wherein the valves D and E are opened and closed by the controller to cause a gas in the cultivation room to reach a preset concentration;
a second combination of settings corresponding to the cock A being open, the valve B being closed, the valve C being closed, and the circulation pump being off, wherein the valves D and E are opened and closed by the controller to cause a gas in the cultivation room to reach a preset concentration; or
a third combination of settings corresponding to the cock A being closed, the circulation pump being on, the fan being on, the valve D being closed, the valve E being closed, wherein the valves B and C are opened and closed by the controller at predetermined intervals such that the valve B is closed when the valve C is open and such that the valve B is open when the valve C is closed, wherein the valve B cannot be closed when the valve C is closed.

2. The incubator according to claim 1, further comprising:
a second filter being included in the third pipe between the cock A and a connection of the third pipe to the second pipe.

3. The incubator according to claim 1, wherein the fan circulates the sterilizing gas in the cultivation room, wherein the controller is connected to the circulation pump and to the fan, the controller operating in a sterilizing mode in which the controller operates both the circulation pump and the fan, wherein the sterilizing mode corresponds to the third combination of settings.

4. The incubator according to claim 1, further comprising the isolator.

5. The incubator according to claim 1, further comprising the sterile gas supply device.

6. An incubator, to be connected to an isolator and at least two cultivation gas supply devices, the incubator comprising:
a controller;
a cultivation room including a first port, a second port, and a third port, the cultivation room configured to be sterilized by a sterilizing gas supplied from a sterile gas supply device connected to the isolator;
a pipe sterilizing unit wherein the sterilizing gas flows from the second port into a second pipe, through the second pipe to a circulation pump, from the circulation pump into at least one path selected from among path (a) or path (b), wherein path (a) corresponds to a first pipe, through a valve C, to a first filter and then to the first port, wherein path (b) corresponds to a fourth pipe, through a valve B, to a third filter and then to the third port, wherein the circulation pump forces the sterilizing gas to flow from the second port to the first port either through the first pipe and the first filter, or through the fourth pipe and the third filter, or through the first pipe and the first filter and also through the fourth pipe and the third filter;

a first cultivation gas control unit comprising a first cultivation gas control pipe, the first cultivation gas control pipe including at one end thereof a first connector to connect to a first cultivation gas supply device, and the other end thereof being coupled to the first pipe, wherein the first pipe is between the first filter and the circulation pump, wherein the first cultivation gas control pipe includes a valve D;

a second cultivation gas control unit comprising a second cultivation gas control pipe, the second cultivation gas control pipe including at one end thereof a second connector to connect to a second cultivation gas supply device, and the other end thereof being coupled to the fourth pipe, wherein the fourth pipe is between the third filter and the circulation pump, wherein the second cultivation gas control pipe includes a valve E;

a third pipe, having a cock A, connected to the second pipe between the second port and the circulation pump;

a fan disposed inside the cultivation room; and a machine room disposed at an outer side of the cultivation room, wherein at least the circulation pump, first pipe, second pipe, and first filter are in the machine room;

wherein the incubator is configured to have:

a first combination of settings corresponding to the cock A being closed, the valve B being closed, the valve C being closed, and the circulation pump being off, wherein the valves D and E are opened and closed by the controller to cause a gas in the cultivation room to reach a preset concentration;

a second combination of settings corresponding to the cock A being open, the valve B being closed, the valve C being closed, and the circulation pump being off, wherein the valves D and E are opened and closed by the controller to cause a gas in the cultivation room to reach a preset concentration; or a third combination of settings corresponding to the cock A being closed, the circulation pump being on, the fan being on, the valve D being closed, the valve E being closed, wherein the valves B and C are opened and closed by the controller at predetermined intervals such that the valve B is closed when the valve C is open and such that the valve B is open when the valve C is closed, wherein the valve B cannot be closed when the valve C is closed.

7. The incubator according to claim 6, further comprising:
a second filter being included in the third pipe between the cock A and a connection of the third pipe to the second pipe.

8. The incubator according to claim 6, wherein the fan circulates the sterilizing gas in the cultivation room, wherein the controller is connected to the circulation pump and to the fan, the controller operating in a sterilizing mode in which the controller operates both the circulation pump and the fan, wherein the sterilizing mode corresponds to the third combination of settings.

9. The incubator according to claim 6, further comprising the isolator.

10. The incubator according to claim 6, further comprising the sterile gas supply device.

* * * * *